United States Patent
Yuille et al.

(10) Patent No.: US 12,327,192 B2
(45) Date of Patent: Jun. 10, 2025

(54) EARLY DETECTION OF PANCREATIC NEOPLASMS USING CASCADED MACHINE LEARNING MODELS

(71) Applicant: The Johns Hopkins University, Baltimore, MD (US)

(72) Inventors: Alan Yuille, Baltimore, MD (US); Seyoun Park, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 376 days.

(21) Appl. No.: 17/775,807

(22) PCT Filed: Nov. 11, 2020

(86) PCT No.: PCT/US2020/060061
§ 371 (c)(1),
(2) Date: May 10, 2022

(87) PCT Pub. No.: WO2021/096991
PCT Pub. Date: May 20, 2021

(65) Prior Publication Data
US 2022/0392641 A1     Dec. 8, 2022

Related U.S. Application Data

(60) Provisional application No. 62/933,946, filed on Nov. 11, 2019.

(51) Int. Cl.
*G06N 3/084*     (2023.01)
*G06T 7/00*     (2017.01)
(Continued)

(52) U.S. Cl.
CPC .......... *G06N 3/084* (2013.01); *G06T 7/0014* (2013.01); *G06V 10/82* (2022.01); *G06V 20/695* (2022.01);
(Continued)

(58) Field of Classification Search
CPC ......... G06T 7/0014; G06T 2207/20081; G06T 2207/20084; G06T 2207/30096
See application file for complete search history.

(56) References Cited

U.S. PATENT DOCUMENTS

| | | | |
|---|---|---|---|
| 9,739,783 B1 | 8/2017 | Kumar et al. | |
| 9,811,906 B1 | 11/2017 | Vizitiu et al. | |
| | (Continued) | | |

FOREIGN PATENT DOCUMENTS

| | | |
|---|---|---|
| CN | 109685809 | 4/2019 |
| EP | 3252671 | 5/2016 |
| | (Continued) | |

OTHER PUBLICATIONS

Extended Search Report in European Appln. No. 20794854.8, dated Apr. 19, 2023, 5 pages.
(Continued)

*Primary Examiner* — John R Wallace
(74) *Attorney, Agent, or Firm* — Fish & Richardson P.C.

(57) ABSTRACT

Methods, systems, and apparatuses, including computer programs for detecting pancreatic neoplasms. A method includes providing an image as an input to a first model, obtaining first output data generated by the first model based on the first model's processing of the image, the first output data representing a portion of the image that depicts a pancreas, providing the first output data as an input to a second model, obtaining second output data generated by the second model based on the second model's processing of the second input data, the second output indicating whether the depicted pancreas is normal or abnormal, providing the first output data and the second output data as an input to a third model, and obtaining third output data generated by the third model, the third output data including data indicating (Continued)

that the pancreas is normal or data indicating a likely location of a pancreatic neoplasm.

17 Claims, 3 Drawing Sheets

(51) Int. Cl.
    *G06V 10/82*     (2022.01)
    *G06V 20/69*     (2022.01)
    *G16H 50/20*     (2018.01)

(52) U.S. Cl.
    CPC ... *G16H 50/20* (2018.01); *G06T 2207/20081* (2013.01); *G06T 2207/20084* (2013.01); *G06T 2207/30096* (2013.01)

(56) References Cited

U.S. PATENT DOCUMENTS

| | | |
|---|---|---|
| 9,947,102 B2 | 4/2018 | Xu et al. |
| 9,965,863 B2 | 5/2018 | Xu et al. |
| 10,140,544 B1 | 11/2018 | Zhao et al. |
| 11,049,250 B2 | 6/2021 | Nye et al. |
| 11,308,623 B2 | 4/2022 | Yuille et al. |
| 2010/0067754 A1 | 3/2010 | Collins et al. |
| 2012/0230572 A1 | 9/2012 | Kohlberger |
| 2015/0003703 A1 | 1/2015 | Franz et al. |
| 2016/0098833 A1 | 4/2016 | Tsadok et al. |
| 2017/0249744 A1 | 8/2017 | Wang et al. |
| 2018/0042565 A1 | 2/2018 | Wilson et al. |
| 2018/0108124 A1 | 4/2018 | Guo et al. |
| 2019/0105009 A1 | 4/2019 | Siemionow et al. |
| 2019/0220975 A1 | 7/2019 | Hsieh et al. |
| 2019/0258878 A1 | 8/2019 | Koivisto et al. |
| 2020/0005899 A1* | 1/2020 | Nicula ............... G16B 40/20 |
| 2020/0202507 A1 | 6/2020 | Ceccaldi et al. |
| 2020/0245960 A1 | 8/2020 | Richter et al. |
| 2020/0278681 A1 | 9/2020 | Gier et al. |
| 2020/0342600 A1 | 10/2020 | Sjostrand et al. |
| 2020/0356899 A1 | 11/2020 | Rejeb Sfar et al. |
| 2020/0372626 A1 | 11/2020 | Dal Mutto et al. |
| 2021/0012505 A1 | 1/2021 | Yuille et al. |
| 2022/0215646 A1 | 7/2022 | Park et al. |
| 2022/0277459 A1 | 9/2022 | Yuille et al. |
| 2024/0290075 A1 | 8/2024 | Yuille et al. |

FOREIGN PATENT DOCUMENTS

| | | | |
|---|---|---|---|
| EP | 3392832 | 10/2018 | |
| WO | WO 2016182551 | 11/2016 | |
| WO | WO 2017210690 | 12/2017 | |
| WO | WO 2018015080 | 1/2018 | |
| WO | WO 2018015414 | 1/2018 | |
| WO | WO 2019005722 | 1/2019 | |
| WO | WO-2019005722 A1 * | 1/2019 | ......... G06F 18/2413 |

OTHER PUBLICATIONS

Hu et al. "Brain Tumor Segmentation Using Multi-Cascaded Convolutional Neural Networks and Conditional Random Field," IEEE Access, Jul. 8, 2019, 7:92615-92629.
Wang et al., "Abdominal Multi-organ Segmentation with Organ-Attention Networks and Statistical Fusion," CoRR, submitted on Apr. 23, 2018, arXiv:1804.08414v1, 21 pages.
Wang et al., English translation of CN 109685809 A, published on Apr. 26, 2019, 14 pages.
Arthur et al., "k-means++: The advantages of careful seeding," Proceedings of the Eighteenth Annual ACM-SIAM Symposium on Discrete Algorithms, Jan. 2007, 1027-1035.
Banerjee et al., "Clustering on the unit hypersphere using von mises-fisher distributions," Journal of Machine Learning Research, Sep. 2005, 6:1345-1382.
Bienenstock et al., "Compositionality, MDL Priors, and Object Recognition," Proceedings of the 9th International Conference on Neural Information Processing Systems, Dec. 1996, 838-844.
Cai et al., "Cascade R-CNN: Delving into High Quality Object Detection," Proceedings of the IEEE/CVF Conference on Computer Vision and Pattern Recognition (CVPR), Jun. 2018, 6154-6162.
Carlson et al., "A Sparse Object Coding Scheme in Area V4," Current Biology, Feb. 22, 2011, 21(4):288-293.
Dai et al., "Unsupervised learning of dictionaries of hierarchical compositional models," Proceedings of the IEEE Conference on Computer Vision and Pattern Recognition, Jun. 2014, 2505-2512.
Deng et al., "ImageNet: A Large-Scale Hierarchical Image Database," Proceedings of the IEEE Conference on Computer Vision and Pattern Recognition, Jun. 2009, 248-255.
DeVries et al., "Improved regularization of convolutional neural networks with cutout," CoRR, submitted on Nov. 29, 2017, arXiv:1708.04552v2, 8 pages.
Fawzi et al., "Measuring the effect of nuisance variables on classifiers," Proceedings of the British Machine Vision Conference (BMVC), Sep. 2016, 12 pages.
Fidler et al., "Learning a hierarchical compositional shape vocabulary for multiclass object representation," CoRR, submitted on Aug. 23, 2014, arXiv:1408.5516v1, 17 pages.
Fodor et al., "Connectionism and cognitive architecture: A critical analysis," Cognition, Mar. 1988, 28(1-2):3-71.
George et al., "A generative vision model that trains with high data efficiency and breaks text-based captchas," Science, Oct. 26, 2017, 358(6368):eaag2612, 19 pages.
Girshick et al., "Rich feature hierarchies for accurate object detection and semantic segmentation," Proceedings of the IEEE Conference on Computer Vision and Pattern Recognition (CVPR), Jun. 2014, 580-587.
Girshick, "Fast R-CNN," Proceedings of the IEEE International Conference on Computer Vision (ICCV), Dec. 2015, 1440-1448.
International Preliminary Report on Patentability in International Appln. No. PCT/US2022/033438, mailed on Dec. 28, 2023, 9 pages.
International Search Report and Written Opinion in International Appln. No. PCT/US2022/033438, mailed on Oct. 20, 2022, 10 pages.
Jin et al., "Context and hierarchy in a probabilistic image model," Proceedings of the 2006 IEEE Computer Society Conference on Computer Vision and Pattern Recognition (CVPR'06), Jun. 2006, 2145-2152.
Kingma et al., "Adam: A method for stochastic optimization," CoRR, submitted on Dec. 22, 2014, arXiv:1412.6980v1, 9 pages.
Kortylewski et al., "Compositional Convolutional Networks For Robust Object Classification under Occlusion," CoRR, submitted on May 29, 2019, arXiv:1905.11826v2, 12 pages.
Kortylewski et al., "Greedy structure learning of hierarchical compositional models," CoRR, submitted on Jan. 22, 2017, arXiv:1701.06171v1, 16 pages.
Kortylewski et al., "Probabilistic compositional active basis models for robust pattern recognition," Proceedings of the British Machine Vision Conference (BMVC), Sep. 2016, 12 pages.
Kortylewski, "Model-based image analysis for forensic shoe print recognition," Dissertation for the Degree of Doctor of Philosophy, University of Basel, Jun. 2017, 124 pages.
Lampert et al., "Beyond sliding windows: Object localization by efficient subwindow search," IEEE Conference on Computer Vision and Pattern Recognition (CVPR), Jun. 2008, 8 pages.
Li et al., "AOGNets: Compositional Grammatical Architectures for Deep Learning," Proceedings of the IEEE/CVF Conference on Computer Vision and Pattern Recognition (CVPR), Jun. 2019, 6220-6230.
Li et al., "SymmNet: A Symmetric Convolutional Neural Network for Occlusion Detection," Proceedings of the British Machine Vision Conference (BMVC), Sep. 2018, 14 pages.
Liao et al., "Learning deep parsimonious representations," Advances in Neural Information Processing Systems, Dec. 2016, 29:5076-5084.
Lin et al., "Microsoft COCO: Common Objects in Context," Computer Vision—ECCV 2014 (LNCS), Sep. 2014, 8693:740-755.

(56) References Cited

OTHER PUBLICATIONS

Reddy et al., "Occlusion-Net: 2D/3D Occluded Keypoint Localization Using Graph Networks," Proceedings of the IEEE/CVF Conference on Computer Vision and Pattern Recognition (CVPR), Jun. 2019, 7326-7335.
Ren et al., "Faster R-CNN: Towards Real-Time Object Detection with Region Proposal Networks," Advances in Neural Information Processing Systems, Dec. 2015, vol. 28, 9 pages.
Roe et al., "Toward a Unified Theory of Visual Area V4," Neuron, Apr. 12, 2012, 74(1):12-29.
Sasikumar et al., "First-pass processing of value cues in the ventral visual pathway," Current Biology, Feb. 8, 2018, 28(4):538-548.
Simonyan et al., "Very deep convolutional networks for large-scale image recognition," CoRR, submitted on Dec. 23, 2014, arXiv:1409.1556v5, 13 pages.
Stone et al., "Teaching Compositionality to CNNs," Proceedings of the IEEE/CVF Conference on Computer Vision and Pattern Recognition (CVPR), Jul. 2017, 5058-5067.
Sun et al., "Symmetric stereo matching for occlusion handling," Proceedings of the IEEE Computer Society Conference on Computer Vision and Pattern Recognition (CVPR), Jun. 2005, 399-406.
Tabernik et al., "Towards deep compositional networks," Proceedings of the 23rd International Conference on Pattern Recognition (ICPR), Dec. 2016, 3470-3475.
Tang et al., "Deeply Learned Compositional Models for Human Pose Estimation," Computer Vision—ECCV 2018 (LNCS), Sep. 2018, 11207:190-206.
Tang et al., "Towards a unified compositional model for visual pattern modeling," Proceedings of the IEEE International Conference on Computer Vision (ICCV), Oct. 2017, 2784-2793.
The Handbook of Brain Theory and Neural Networks, 2nd ed., Arbib (ed.), 2003, pp. 244-248.
Vaziri et al., "A channel for 3d environmental shape in anterior inferotemporal cortex," Neuron, Oct. 2014, 84(1):55-62.
Wang et al., "Detecting semantic parts on partially occluded objects," Proceedings of the British Machine Vision Conference (BMVC), Sep. 2017, 13 pages.
Wang et al., "Discovering Internal Representations from Object-CNNs Using Population Encoding," CoRR, submitted on Nov. 21, 2015, arXiv:1511.06855v1, 12 pages.
Wang et al., "Visual concepts and compositional voting," CoRR, submitted on Nov. 13, 2017, arXiv:1711.04451v1, 37 pages.
Xiang et al., "Beyond Pascal: A benchmark for 3D object detection in the wild," IEEE Winter Conference on Applications of Computer Vision, Mar. 2014, 75-82.
Xiang et al., "Object Detection by 3D Aspectlets and Occlusion Reasoning, " IEEE International Conference on Computer Vision Workshops, Dec. 2013, 530-537.
Xiao et al., "Tdapnet: Prototype network with recurrent top-down attention for robust object classification under partial occlusion," CoRR, submitted on Sep. 9, 2019, arXiv:1909,03879v1, 11 pages.
Yamane et al., "A neural code for three-dimensional object shape in macaque inferotemporal cortex," Nature Neuroscience, Oct. 5, 2008, 11(11):1352-1360.
Yan et al., "Inferring occluded features for fast object detection," Signal Processing, May 2015, 110:188-198.
Yun et al., "CutMix: Regularization Strategy to Train Strong Classifiers with Localizable Features," CoRR, submitted on May 13, 2019, arXiv:1905.04899v1, 14 pages.
Zhang et al., "Deepvoting: A robust and explainable deep network for semantic part detection under partial occlusion," Proceedings of the IEEE/CVF Conference on Computer Vision and Pattern Recognition (CVPR), Jun. 2018, 1372-1380.
Zhang et al., "Interpretable convolutional neural networks," Proceedings of the IEEE/CVF Conference on Computer Vision and Pattern Recognition (CVPR), Jun. 2018, 8827-8836.
Zhang et al., "Occlusion-aware R-CNN: Detecting Pedestrians in a Crowd," CORR, submitted on Jul. 23, 2018, arXiv:1807.08407v1, 17 pages.
Zhu et al., "Robustness of Object Recognition under Extreme Occlusion in Humans and Computational Models," Proceedings of the 41st Annual Meeting of the Cognitive Science Society: Creativity + Cognition + Computation, Jul. 2019, 7 pages.
Zhu et al., "Unsupervised Structure Learning: Hierarchical Recursive Composition, Suspicious Coincidence and Competitive Exclusion," Computer Vision—ECCV 2008 (LNCS), Oct. 2008, 5303:759-773.
Abraham et al., "Extracting Brain Regions from Rest fMRI with Total-Variation Constrained Dictionary Learning," MICCAI., 2013, 16:2:607-15.
Ansari et al. "Role of Magnetic Resonance Imaging in the Detection and Characterization of Solid Pancreatic Nodules: An Update." World Journal of Radiology, 28, 7(11), Nov. 2015, 361-374.
Asman et al., "Formulating spatially varying performance in the statistical fusion framework," IEEE Trans. On Med, Imaging, 2012, 31:6:1326-1336.
Asman et al., "Non-local statistical label fusion for multi-atlas segmentation," Med. Image Anal., Feb. 2013, 17:2:194-208.
Aydogan et al., "Analysis of Trabecular Bone Microstructure Using Contour Tree Connectivity, " MICCAI., 2013, 16:2:428-35.
Bieth et al., "Atlas Construction for Dynamic (4D) Pet Using Diffeomorphic Transformations, " MICCAI, 2013, 35-42.
Boykov et al., "Fast approximate energy minimization via graph cuts," IEEE Transactions on PAMI, 2001, 23:11:122-1239.
Brosch et al., "Manifold Learning of Brain MRIs by Deep Learning," MICCAI., 2013, 16:2:633-40.
Cerrolaza et al., "Multiresolution Hierarchical Shape Models in 3D Subcortical Brain Structures, " MICCAI., 2013, 16:2:641-8.
Chang et al., "Characterization of Tissue Histopathology via Predictive Sparse Decomposition and Spatial Pyramid Matching," MICCAI, 2013, 8150:91-98.
Chatelain et al., "Learning from Multiple Experts with Random Forests: Application to the Segmentation of the Midbrain in 3D Ultrasound," MICCAI, 2013, 16:2:230-7.
Chen et al., "Attention to scale: Scale-aware semantic image segmentation," In proceedings of the IEEE conf. on CCVPR, 2016, 3640-3649.
Chen et al., "DeepLab: Semantic Image Segmentation with Deep Convolutional Nets, Atrous Convolution, and Fully Connected CRFs", IEEE Transactions on Pattern Analysis and Machine Intelligence, 2016, 40(4): 834-848.
Chen et al., "VoxResNet:Deep voxelwise residual networks for brain segmentation from 3D MR images, " NeuroImage, 2018, 170:446-455.
Chu et al., "Multi- organ segmentation based on spatially-divided probabilistic atlas from 3D abdominal CT images," Lecture Notes in Comp. Sci., 2013, 8150LNCS(part 2) 165-172.
Ciompi et al., "Stent Shape Estimation through a Comprehensive Interpretation of Intravascular Ultrasound Images, " MICCAI, 2013, 16:2:345-52.
Ciresan et al., "Mitosis Detection in Breast Cancer Histology Images with Deep Neural Networks," MICCAI., 2013, 16:2:411-8.
Cisek et al., "3D U-Net: Learning dense volumetric segmentation from sparse annotation," MICCAI, 2016, 424-432.
Cruz-Roa et al., "A Deep Learning Architecture for Image Representation, Visual Interpretability and Automated Basal-Cell Carcinoma Cancer Detection," MICCAI., 2013, 16:2:403-10.
Da Mota et al., "Enhancing the Reproducibility of Group Analysis with Randomized Brain Parcellations, " MICCAI., 2013, 16:2:591-8.
Datar et al., "Geodesic Distances to Landmarks for Dense Correspondence on Ensembles of Complex Shapes," MICCAI., 2013, 16:19-26.
De Silva et al., "Improving 2D-3D Registration Optimization Using Learned Prostate Motion Data," MICCAI, 2013, 16:2:124-31.
Dinse et al., "A Histology-Based Model of Quantitative T1 Contrast for In-vivo Cortical Parcellation of High-Resolution 7 Tesla Brain MR Images,".
Dou et al., "3D deeply supervised network for automatic liver segmentation from CT volumes," Med. Image Analysis, Oct. 2017, 41:40-54.

(56) References Cited

OTHER PUBLICATIONS

Dou et al., "Multilevel Contextual 3-D CNNs for False Positive Reduction in Pulmonary Nodule Detection", IEEE Tbe, 2017, 64(7): 1558-1567.
Durichen et al., "Respiratory Motion Compensation with Relevance Vector Machines," MICCAI., 2013, 108-115.
Everingham et al., The PASCAL visual object classes challenge 2012 (VOC2012) results. 2012, Pascal2, 24 pages.
Farag et al., "Automatic pancreas segmentation using coarse to-fine superpixel labeling," Deep learning ans Convutional Neural Networks for Medical Computing, 2017.
Forman et al., "Free-Breathing Whole-Heart Coronary MRA: Motion Compensation Integrated into 3D Cartesian Compressed Sensing Reconstruction," MICCAI., 2013, 16:2:575-82.
Gao et al., "Incremental Learning with Selective Memory (ILSM): Towards Fast Prostate Localization for Image Guided Radiotherapy," MICCAI., 2013, 16:2:378-386.
Gibson et al., "Automatic multi-organ segmentation on abdominal CT with dense V- networks," IEEE Trans. Med. Imaging, Aug. 2018, 37:8:1822-1834.
Ginsburg et al., "Variable Importance in Nonlinear Kernels (VINK): Classification of Digitized Histopathology," MICCAI., 2013, 16:2:238-45.
Glocker et al., "Vertebrae Localization in Pathological Spine CT via Dense Classification from Sparse Annotations," MICCAI., 2013, 16:2:262-70.
Gomez et al., "3D Intraventricular Flow Mapping from Colour Doppler Images and Wall Motion," MICCAI,2013, 16:2:476-83.
Grbic et al., "Image-Based Computational Models for TAVI Planning: From CT Images to Implant Deployment," MICCAI., 2013, 16:2:395-402.
Hacihaliloglu e et al., "Statistical Shape Model to 3D Ultrasound Registration for Spine Interventions Using Enhanced Local Phase Features," MICCAI., 2013, 16:2:361-8.
Hamy et al., "Respiratory Motion Correction in Dynamic-MRI: Application to Small Bowel Motility Quantification during Free Breathing," MICCAI, 2013, 16:2:132-40.
Havaei et al., "Brain tumor segmenation with deep neural networks," Medical Image analysis, Jan. 2017, 35:18-31.
He et al., "Deep Residual Learning for Image Recognition", 2016, CVPR, 770-778.
Heimann et al., "Comparison and evaluation of methods for live segmentation from CT datasets," IEEE Transactions on Medical Imaging, Aug. 2009, 28:8:1251-1265.
Hibar er al., "Genetic Clustering on the Hippocampal Surface for Genome-Wide Association Studies," MICCAI., 2013, 16:2:690-7.
Hu et al., "Automated Separation of Binary Overlapping Trees in Low-Contrast Color Retinal Images, " MICCAI., 2013, 16:2:436-43.
Huang et al., "A New Sparse Simplex Model for Brain Anatomical and Genetic Network Analysis, " MICCAI., 2013, 16:2:625-632.
Huh et al., "Apoptosis Detection for Non-adherent Cells in Time-lapse Phase Contrast Microscopy," MICCAI, 2013, 8150: 59-66.
Hussein et al., "Lung and Pancreatic Tumor Characterization in the Deep Learning Era: Novel Supervised and Unsupervised Learning Approaches", IEEE Transactions on Medical Imaging, 2019, 38(8): 1777-1787.
Hussein et al., "Supervised and unsupervised tumor characterization in the deep learning era," ArXiv, 2018.
Iglesias et al., Multi-atlas segmentation of biomedical images: A survey, Med Image Anal., Aug. 2015, 24:1:205-219.
Imani et al., "Ultrasound-Based Characterization of Prostate Cancer: An in vivo Clinical Feasibility Study," MICAAI, 2013, 16:2:279-86.
International Preliminary Report on Patentability in Appl. No. PCT/US2020/029631, dated Sep. 28, 2021, 6 pages.
International Preliminary Report on Patentability in International Application No. PCT/US2020/060061, mailed on May 27, 2022, 9 pages.
International Search Report and Written Opinion in International Application No. PCT/US2020/060061, mailed on Mar. 1, 2021, 14 pages.
International Search Report in Appl. No. PCT/US2020029631, dated Jul. 30, 2020, 6 pages.
Jiang et al., "Predictive Models of Resting State Networks for Assessment of Altered Functional Connectivity in MCI," MICCAI, 2013, 16:2:674-81.
Jimenez del Toro et al., "Epileptogenic Lesion Quantification in MRI Using Contralateral 3D Texture Comparisons," MICCAI., 2013, 16:2:353-60.
Kamnitsas et al., "Efficient multi-scale 3D CNN with fully connected CRF for accurate brain lesion segmentation," Med. Image Analysis, Feb. 2017, 36:61-78.
Karasawa e al., "Multi-atlas pancreas segmentation: Atlas selection based on vessel structure," Med. Image Analysis, 2017, 39:18-28.
Kirbas et al., "A review of vessel extraction techniques and algorithms," ACM Computing Surveys, 2004, 36:2:81-121.
Koenig et al., "The Spatial Periodicity of Grid Cells Is Not Sustained During Reduced Theta Oscillations," Science, 2011, 332:592-595.
Kong et al., "RON: Reverse connection with objectness prior networks for object detection," IEEE Conference on Computer Vision Pattern Recognition, Jul. 2017, 5936-5944.
Kortylewski et al., "Compositional Convolutional Neural Networks: A Deep Architecture with Innate Robustness to Partial Occlusion," arXiv:2003.04490v3, Apr. 2020, 10 pages.
Krizkevsky et al., "ImageNet Classification with Deep Convolutional Neural Networks", NIPS, 9 pages, 2012.
Kroeger et al., "Learning to Segment Neurons with Non-local Quality Measures," MICCAI., 2013, 16:2:419-27.
Kronman et al., "Image Segmentation Errors Correction by Mesh Segmentation and Deformation," MICCAI., 2013, 206-213.
Kwitt et al., "Studying Cerebral Vasculature Using Structure Proximity and Graph Kernels," MICCAI., 2013, 16:2:534-541.
Lesage et al., "A review of 3D vessel lumen segmentation techniques: Models, features and extraction schemes," SciDirect., 2009, 13:819-845.
Li et al., "Automatic liver segmentation based shape constraints and deformable graph cut in CT images," IEEE tans. On Image Proc., Dec. 2015, 24:12.
Liao et al., "Representation Learning: A Unified Deep Learning Framework for Automatic Prostate MR Segmentation," MICCAI., 2013, 16:2:254-61.
Lindner et al., "Accurate Bone Segmentation in 2D Radiographs Using Fully Automatic Shape Model Matching Based On Regression-Voting," MICCAI., 2013, 181-189.
Liu et al., "Automatic pancreas segmentation via coarse location and ensemble learning," IEEE Access, 2019, 9 pages.
Liu et al., "High-Order Graph Matching Based Feature Selection for Alzheimer's Disease Identification," MICCAI, 2013, 16:2:311-318.
Liu et al., "A Variational Framework for Joint Detection and Segmentation of Ovarian Cancer Metastases," MICCAI., 2013, 8150:83-90.
Liu et al., "Joint shape representation and classification for detecting PDAC," MLMI@MICCAI, 2019.
Liu et al., "Longitudinal Modeling of Glaucoma Progression Using 2-Dimensional Continuous-Time Hidden Markov Model," MICCAI., 2013, 16:2:444-451.
Liu et al., "Multifold Bayesian Kernelization in Alzheimer's Diagnosis," MICCAI., 2013, 16:2:303-10.
Liu et al., "Tracking of Carotid Arteries in Ultrasound Images," MICCAI., 2013, 16:2:526-33.
Lombaert et al., "Joint Statistics on Cardiac Shape and Fiber Architecture," MICCAI., 2013, 16:2:492-500.
Long et al., "Fully Convolutional Networks for Semantic Segmentation," CVPR, 2015, 3431-3440.
Lorenzi et al., "Sparse Scale-Space Decomposition of Volume Changes in Deformations Fields," MICCAI., 2013, 16:2:328-35.
Lorza et al., "Carotid Artery Lumen Segmentation in 3D Free-Hand Ultrasound Images Using Surface Graph Cuts," MICCAI., 2013, 16:2: 542-9.

(56) References Cited

OTHER PUBLICATIONS

Lugo-fagundo et al., "Deep learning in radiology: Now the real work begins," J. Am. Coll. Radiol., Feburary 2018, 15:2:364-367.
Lundervold et al., "An overview of deep learning in medical imaging focusing on MRI," Zeitschrift für Medizinische Physik, May 2019, 29:2:102-127.
Lv et al., "Group-Wise FMRI Activation Detection on Corresponding Cortical Landmarks," MICCAI., 2013, 16:2:665-73.
Lv et al., "Modeling Dynamic Functional Information Flows on Large-Scale Brain Networks," MICCAI., 2013, 698-705.
Mahapatra et al., "Semi-Supervised and Active Learning for Automatic Segmentation of Crohn's Disease," MICCAI., 2013, 16:2:214-21.
Mahrooghy et al., "Heterogeneity Wavelet Kinetics from DCE-MRI for Classifying Gene Expression Based Breast Cancer Recurrence Risk," MICCA., 2013, 16:2:295-302.
Maier et al, "A gentle introduction to deep learning in medical imaging processing," J. of Med. Physics, Dec. 2018.
Marreiros et al., "Non-rigid Deformation Pipeline for Compensation of Superficial Brain Shift," MICCAI., 2013, 16:2:141-8.
McLeod et al., "Spatio-temporal Dimension Reduction of Cardiac Motion for Group-Wise Analysis and Statistical Testing," MICCAI., 2013, 16:2:501-8.
Melbourne et al., "Measurement of Myelin in the Preterm Brain: Multi-compartment Diffusion Imaging and Multi-component T2 Relaxometry," MICCAI., 2013, 16:2:336-44.
Mharib et al., "Survey on liver CT image segmentation methods," Artif Intell rev., 2012, 37:83-95.
Milletari et al., "V-Net: Fully Convolutional Neural Networks for Volumetric Medical Image Segmentation", 2016 Fourth International Conference on 3D Vision,2016, 565-571.
Mori et al., Medical Image computing and computer-assisted intervention-MICCAI 2013, 16th Int. Conf., Sep. 2013, 36 pages.
Nascimento et al., Multi-atlas segmentation using manifold learning with deep belief neworks, IEE, 2016, 4 pages.
NCBI.gov [online], "Pancreatic cancer treatment (adult) (PDQ)," May 15, 2020, retrieved on Oct. 5, 2020, retrieved from URL<https://www.ncbi.nlm.nih.gov/books/NBK65957/?report-printable. 37 pages.
Nouranian et al., "An Automatic Multi-atlas Segmentation of the Prostate in Transrectal Ultrasound Images Using Pairwise Atlas Shape Similarity," MICCAI, 2013, 16:2:173-80.
Okada et al., "Abdominal multi-organ segmentation from CT images using conditional shape-location and unsupervised intensity priors," Med. Image Anal., Dec. 2015, 26:1:1-18.
Oktay et al., "Biomechanically driven registration of pre- to intra-operative 3D images for laparoscopic surgery," MICCAI., 2013, 16:2:1-9.
Ospina et al., "A Tensor-Based Population Value Decomposition to Explain Rectal Toxicity after Prostate Cancer Radiotherapy," MICCAI., 2013, 16:2:387-94.
Petersen et al., "Quantitative Airway Analysis in Longitudinal Studies Using Groupwise Registration and 4D Optimal Surfaces," MICCAI., 2013, 16:2:287-94.
Piuze et al., "Cardiac Fiber Inpainting Using Cartan Forms," MICCAI, 2013, 16:2:509-17.
Porras et al., "Myocardial Motion Estimation Combining Tissue Doppler and B-mode Echocardiographic Images, " MICCAI., 2013, 16:2:484-91.
Prasoon et al., "Deep Feature Learning for Knee Cartilage Segmentation Using a Triplanar Convolutional Neural Network," MICCAI., 2013, 16:2:246-53.
Prevost et al., "Registration of Free-Breathing 3D+t Abdominal Perfusion CT Images via Co-segmentation," MICCAI, 2013, 16:2:99-107.
Qiu et al., "Fast Globally Optimal Segmentation of 3D Prostate MRI with Axial Symmetry Prior," MICCAI., 2013, 16:2:198-205.
Rafii-Tari et al., "Learning-Based Modeling of Endovascular Navigation for Collaborative Robotic Catheterization," MICCAI., 2013, 16:2:369-77.
Rajchl et al., "Deepcut: Object segmentation from bounding box annotations using convulutional neural networks," IEE Trans. Med. Imaging., 2016, 10 pages.
Romain et al., "A Multi-task Learning Approach for Compartmental Model Parameter Estimation in DCE-CT Sequences,"MICAA., 2013, 16:2:271-8.
Ronneberger et al., "U-Net: Convolutional Networks for Biomedical Image Segmentation", MICCAR, 234-241, 2015.
Roth et al., "Deep convolutional networks for pancreas segmentation in CT imaging," SPIE Med., Imaging, 2015, 9413-94131G.
Roth et al., "DeepOrgan: Multi-level Deep Convolutional Networks for Automated Pancreas Segmentation", MICCAI, 556-564, 2015.
Roth et al., "Hierarchical 3D fully convolutional networks for multi-organ segmentation," ARXIV., Apr. 2017, arXiv:1704.06382:11 pages.
Roth et al., Spatial aggregation of holistically-nested convolutional neural networks for automated pancreas localization and segmentation, Medical Image Analysis, Apr. 2018, 45:94-107.
Roth et al., "Spatial Aggregation of Holistically-Nested Networks for Automated Pancreas Segmentation", 2016, MICCAI, 451-459.
Roth et al., "Towards dense volumetric pancreas segmentation in CT using 3D fully conventional networks," Medical Imaging, 2018, 6 pages.
Sabuncu et al., "A generative model for image segmentation based on label fusion," IEE Trans. On Med. Imaging, Oct. 2010, 29:10:1714-1729.
Saito et al., "Joint optimization of segmentation and shape prior from level-set-based statistical shape model, and its application to the automated segmentation of abdominal organs," Med. Image Analysis, 2016, 28:46-65.
Seito et al., "Pulmonary nodule detection in CT images: False positive reduction using multi-view convolutional networks," IEE Trans. On Med. Imag., May 2016, 35:5:1160-1169.
Shen et al., "A Spatial Mixture Approach to Inferring Sub-ROI Spatio-temporal Patterns from Rapid Event-Related fMRI Data," MICCAI., 2013, 16:2:657-64.
Shen et al., Deep learning in medical image analysis, Annu rev. Biomed. En., 2017, 19:221-248.
Simpson et al., "A bayesian approach for spatially adaptive regularisation in Non-rigid registration," MICCAI., 2013, 10-18.
Song et al., "Discriminative Data Transform for Image Feature Extraction and Classification," MICCAI., 2013, 16:2:452-9.
Suk et al., "Deep Learning-Based Feature Representation for AD/MCI Classification," MICCAI., 2013, 16:2:583-90.
Tang et al., "Random Walks with Efficient Search and Contextually Adapted Image Similarity for Deformable Registration," MICCAI, 2013, 43-50.
Tong et al., "Multiple Instance Learning for Classification of Dementia in Brain MRI," Med. Image Anal., Jul. 2014, 18:5:808-18.
Uzunbas et al., "Collaborative Multi Organ Segmentation by Integrating Deformable and Graphical Models," MICCAI, 2013, 157-164.
Vincent et al., "Bayesian Joint Detection-Estimation of Cerebral Vasoreactivity from ASL fMRI Data," MICCAI, 2013, 616-624.
Wang et al., "Image quality assessment: Form error visibility to structural similarity," IEE. Trans. On Image. Proces., Apr. 2004, 13:4:600-612.
Wang et al., "Interactive Retinal Vessel Extraction by Integrating Vessel Tracing and Graph Search," MICCAI., 2013, 16:2:567-74.
Wang et al., "Automated Embryo Stage Classification in Time-Lapse Microscopy Video of Early Human Embryo Development," MICCAI., 2013, 16:2:460-7.
Wang et al., "Image Quality Assessment: From Error Visibility to Structural Similarity," IEEE Transactions on Image Processing, Apr. 2004, 13:4:600-612.
Wang et al., "Robust Object Detection under Occlusion with Context-Aware CompositionalNets," 2020 IEEE/CVF Conference on Computer Vision and Pattern Recognition (CVPR), Jun. 2020, pp. 12642-12651.
Wang et al., "Sequential Monte Carlo Tracking for Marginal Artery Segmentation on CT Angiography by Multiple Cue Fusion," MICCAI., 2013, 16:2:518-525.

(56) References Cited

OTHER PUBLICATIONS

Wang et al., "Abdominal multi-organ segmentation with organ-attention networks and statistical fusion," Medical Image Analysis, 2019, 55:88-102.
Warfield et al., "Simultaneous truth and performance level estimation (STAPLE): An algorithm for the validation of image segmentation," IEE Trans. Med. Imaging., Jul. 2004, 23:7:903-921.
Wasza et al., "Real-Time Respiratory Motion Analysis Using Manifold Ray Casting of Volumetrically Fused Multi-view Range Imaging," MICCAI., 2013, 16:2:116-23.
Wee et al., "Identification of MCI Using Optimal Sparse MAR Modeled Effective Connectivity Networks," MICCAI., 2013, 16:2:319-327.
Wolz et al., "Automated abdominal multi-organ segmentation with subject-specific atlas generation," IEE Trans. On Med. Imaging, Sep. 2013, 32:9:1723-1730.
Wu et al., "Unsupervised Deep Feature Learning for Deformable Registration of MR Brain Images," MICCAI., 2013, 16:2:649-56.
Xia et al., "Bridging the Gap Between 2D and 3D Organ Segmentation with Volumetric Fusion Net", MICCAI, 445-453, 2018.
Xie et al., "Holistically-Nested Edge Detection", Proceedings of the IEEE International Conference on Computer Vision, 2015, 1395-1403.
Xu et al., "A Symmetric 4D Registration Algorithm for Respiratory Motion Modeling," MICCAI., 2013, 16:2:149-56.
Xu et al., "Automatic Grading of Nuclear Cataracts from Slit-Lamp Lens Images Using Group Sparsity Regression," MICCAI., 2013, 16:2:468-75.
Xu et al., "Spatially Constrained Random Walk Approach for Accurate Estimation of Airway Wall Surfaces," MICCAI., 2013, 16:2:559-566.
Ye et al., "Pathological Site Retargeting under Tissue Deformation Using Geometrical Association and Tracking, " MICCAI., 2013, 16:2:67-74.
Yokota et al., "Automated CT Segmentation of Diseased Hip Using Hierarchical and Conditional Statistical Shape Models," MICCAI, 2013 190-197.
Yoldemir et al., "Overlapping Replicator Dynamics for Functional Subnetwork Identification," MICCAI., 2013, 16:2:682-9.
Yu et al., "Recurrent saliency transformation network: incorporating multi-stage visual cues for small organ segmentation," Arxiv, 2017.
Yuille et al., "Abdominal multi-organ segmentation with organ-attention networks and statistical fusion," Med., Image Anal., Jul. 2019, 55:88-102.
Zhang et al., "Large Deformation Diffeomorphic Registration of Diffusion-Weighted Images with Explicit Orientation Optimization".
Zhang et al., "Personalized Pancreatic Tumor Growth Prediction via Group Learning", MICCAI, 2017, 424-432.
Zhao et al., "Hierarchical Constrained Local Model Using ICA and Its Application to Down Syndrome Detection," MICCAI., 2013, 16:2:222-9.
Zheng et al., "Optic disc and cup segmentation from color fundus photograph using graph cut with priors," MICCAI., 2013, 16:75-82.
Zhou et al., "A Fixed-Point Model for Pancreas Segmentation in Abdominal CT Scans", MICCAI,2017, 693-701.
Zhou et al., "Deep Supervision for Pancreatic Cyst Segmentation in Abdominal CT Scans", MICCAI, 2017, 222-230,.
Zhou et al., "Pancreas Segmentation in Abdominal CT Scan: A Coarse-to-Fine Approach." arXiv:1612.08230v1, Dec. 2016, pp. 1-13.
Zhu et al., "A 3D Coarse-to-Fine Framework for Volumetric Medical Image Segmentation", International Conference on 3D Vision, 682-690, 2018.
Zhu et al., "Deep Learning Representation using Autoencoder for 3D Shape Retrieval", Neurocomputing 204: 41-50, 2016.
Zhu et al., "Multi-scale coarse-to-fine segmentation for screening pancreatic ductal adenocarcinoma," ArXiv, 2019.
Zhu et al., "Random Walks with Adaptive Cylinder Flux Based Connectivity for Vessel Segmentation," MICCAI., 2013, 16:2:550-8.
Zhuang et al., Multi-scale patch and multi-modality atlases for whole heart segmentation of MRI, Med Image Analysis, 2016, 31:77-87.
Zu et al., "Robust multi-atlas propagation by deep sparse representation," Pattern Recognition, 2017, 63:511-517.
Cen et al., "Boosting occluded image classification via subspace decomposition-based estimation of deep features," IEEE Transactions on Cybernetics, Aug. 12, 2019, 50(7):3409-22.
Cen et al., "Deep feature augmentation for occluded image classification," Pattern Recognition, Mar. 1, 2021, 111:107737.
Enzweiler et al., "Multi-cue pedestrian classification with partial occlusion handling," In 2010 IEEE Computer Society Conference on Computer Vision and Pattern Recognition, Jun. 13, 2010, 990-997.
Kortylewski et al., "Combining compositional models and deep networks for robust object classification under occlusion," In Proceedings of the IEEE/CVF Winter Conference on Applications of Computer Vision, 2020, 1333-1341.
Yoo, "Deep convolution neural networks in computer vision: a review," IEIE Transactions on Smart Processing and Computing, Feb. 2015, 4(1):35-43.

\* cited by examiner

EARLY DETECTION OF PANCREATIC NEOPLASMS USING CASCADED MACHINE LEARNING MODELS

CROSS-REFERENCE TO RELATED APPLICATIONS

This application is a National Stage application under 35 U.S.C. § 371 of International Application No. PCT/US2020/060061 having an International Filing Date of Nov. 11, 2020, which claims the benefit of U.S. Provisional Patent Application No. 62/933,946 filed on Nov. 11, 2019, which are incorporated herein by reference in their entirety.

BACKGROUND

Pancreatic cancer is difficult to detect in its early stages. Pancreatic neoplasms cannot be seen or felt by a heath care provider because the pancreas is deep inside the body. People typically do not have symptoms until the pancreatic neoplasms have become very large or has spread to other organs.

SUMMARY

According to one innovative aspect a method for detecting pancreatic neoplasms using cascaded machine learning models is disclosed. In one aspect, the method can include actions of providing first input data to a first machine learning model, the first input data including data representing an image, obtaining first output data generated by the first machine learning model based on the first machine learning model's processing of the first input data, the first output data representing a portion of the image that depicts a pancreas, providing second input data to a second machine learning model, the second input data including the first output data, obtaining second output data generated by the second machine learning model based on the second machine learning model's processing of the second input data, the second output representing data that indicates whether the depicted pancreas is (i) normal or (ii) abnormal, providing third input data to a third machine learning model, the third input data including (i) first output data and (ii) the second output data, and obtaining third output data generated by the third machine learning model, the third output data that includes (a) data indicating that the pancreas is normal or (b) data indicating a likely location of one or more pancreatic neoplasms.

Other versions include corresponding systems, apparatus, and computer programs to perform the actions of methods defined by instructions encoded on computer readable storage devices.

According to another innovative aspect of the present disclosure, another method for detecting pancreatic neoplasms using cascaded machine learning models is disclosed. In one aspect, the method can include actions of providing first input data to a first machine learning model, the first input data including data representing an image, obtaining first output data generated by the first machine learning model based on the first machine learning model's processing of the first input data, the first output data representing a portion of the image that depicts a pancreas, providing second input data to a second machine learning model, the second input data including the data representing a portion of the image that depicts the pancreas, obtaining second output data generated by the second machine learning model based on the second machine learning model's processing of the second input data, the second output data representing data that indicates whether the depicted pancreas is (i) normal or (ii) abnormal, providing third input data to a third machine learning model, the third input data including (i) the data representing a portion of the image that depicts the pancreas and (ii) the data that indicates whether the depicted pancreas is (i) normal or (ii) abnormal, and obtaining third output data generated by the third machine learning model, the third output data including (a) data indicating that the pancreas is normal or (b) data indicating a likely location of one or more pancreatic neoplasms.

Other versions include corresponding systems, apparatus, and computer programs to perform the actions of methods defined by instructions encoded on computer readable storage devices.

DETAILED DESCRIPTION

The present disclosure relates to a system, method, and computer program, for using cascaded machine learning models to facilitate early detection of pancreatic neoplasms. The present disclosure facilitates early detection of pancreatic cancer by analyzing one or more internal images of a body such as CT images. Each particular cascaded machine learning model can function as a separate processing engine that is uniquely configured to perform an operation on particular input data and generate particular output data. Output data generated by a first machine learning model of the cascaded machine learning models is then used in one or more subsequent determinations by one or more subsequent machine learning models in order to determine whether a pancreas depicted in an image has one or more pancreatic neoplasms.

The present disclosure provides multiple technical advantages over conventional systems. In particular, the present disclosure can provide early detection of certain types of neoplasms, which may be cancerous, before the neoplasms are big enough to be visually identified. For example, in some implementations, the present disclosure can include detection of pancreatic neoplasms before the pancreatic neoplasms become too large, before the pancreatic neoplasms spread to other organs, or a combination thereof. Early detection of these neoplasms before the neoplasms grow too large or spread to other organs can result in an earlier selection and administration of a treatment that can be used to prolong the life of an organism such as a human.

Figure 1:
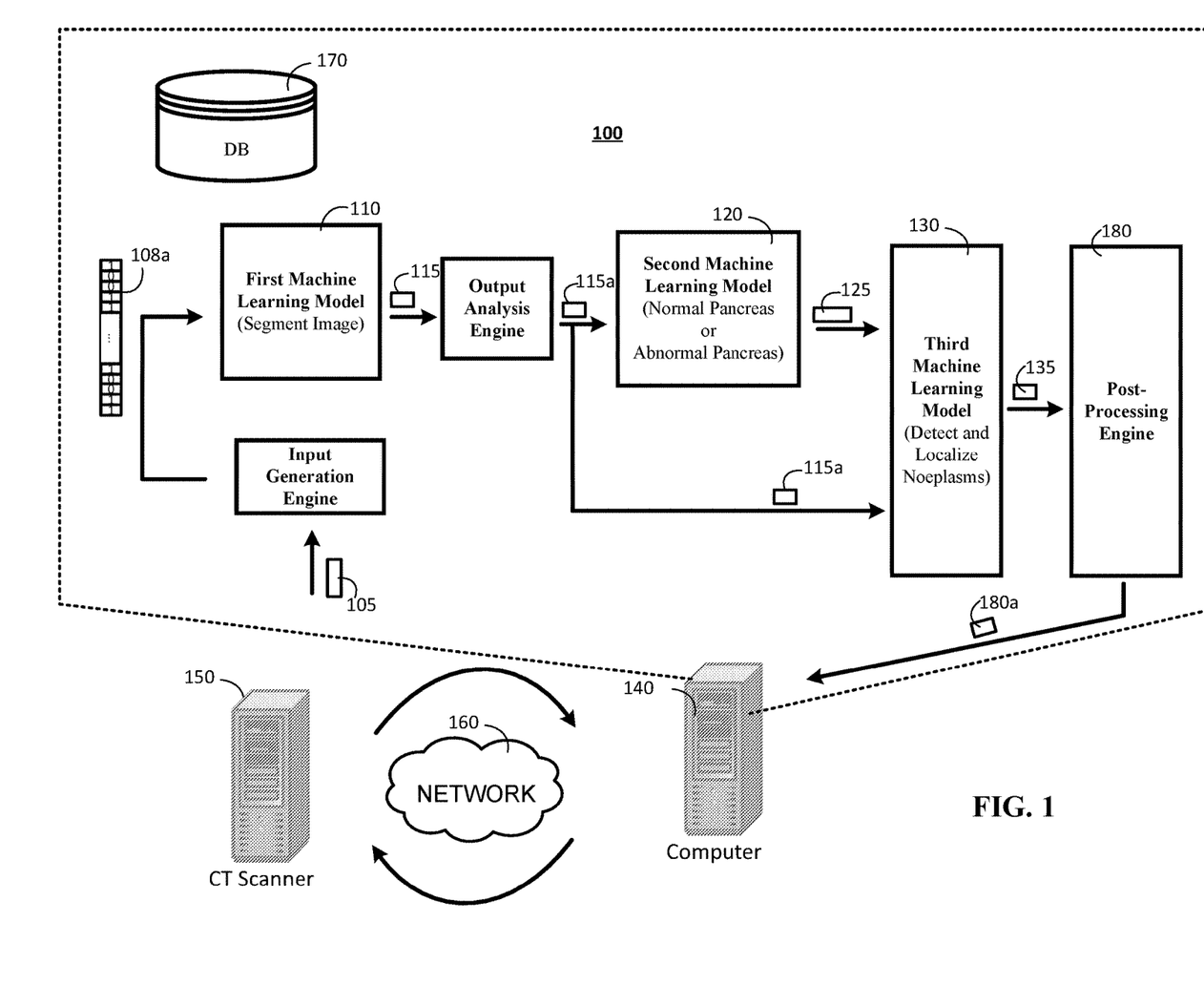
FIG. 1 is a block diagram of an example of a system that uses cascaded machine learning models to facilitate early detection of pancreatic neoplasms.

FIG. 1 is a block diagram of an example of a system 100 that uses cascaded machine learning models to facilitate early detection of pancreatic neoplasms. The system 100 can include an input generation engine 108, a first machine learning model 110, a second machine learning model 120, a third machine learning model 130, and a post processing engine 180. In the example of FIG. 1, the input generation engine 108, the first machine learning model 110, the second machine learning engine 120, the third machine learning engine 130, the database 170, and the post-processing engine 180 are shown as being hosted by the computer 140.

However, the present disclosure is not so limited. In other implementations, for example, computer 140 can be multiple computers. In such implementations, the input generation engine 108, the first machine learning model 110, the second machine learning model 120, the third machine learning model 130, the database 170, and the post-processing engine 180 can be stored across multiple different computers that are networked together via one or more networks. By way of another example, one or more of the input generation engine 108, the first machine learning model 110, the second machine learning model 120, the third machine learning model 130, the database 170, the post-processing engine 180, or any combination thereof may be hosted by the CT-Scanner 150. In such implementations, the CT-Scanner 150 can execute the system 100 as an end-to-end process by generating an image of an internal portion of a person's body, processing the image through the cascaded models and/or engines of system 100, and generating output data indicating whether the system 100 detected the presence of neoplasms. Though an example of a CT-Scanner 150 is described herein, the present disclosure can be use any imaging scanner to generate any image of an internal portion (e.g., one or more organs) of an organism. Likewise, the system 100 can be used to analyze any image of an internal portion of an organism generated by any scanner.

In the example of FIG. 1, the computer 140 obtain an image 105 such as a computed tomography (CT) scan image of an inside portion of an organism's body. The image can be obtained from a device 150 using one or more networks 160. The network 160 can include a wired Ethernet network, a wired optical network, a wireless WiFi network, a LAN, a WAN, a cellular network, the Internet, or any combination thereof. However, the present disclosure is not limited to receipt of the image 105 using one or more networks 160. Instead, in some implementations, the entire system 100 can be implemented within the CT-Scanner 150 or other type of scanner. In such implementations, the image 105 can be obtained from a memory device of the CT-Scanner 150 after generation of the image by the CT-scanner. The device 150 can be a device that generated the image such as a CT scanner. Alternatively, the device 150 can be a device that receives the CT image from the CT scanner. In other implementations, the computer 140 can obtain an image 105 from local storage such as a local database 170 stored in a storage unit of the computer 140, local flash drive, or the like.

In some implementations, the computer 140 can use an input generation engine 108 to perform one or more pre-processing operations on the obtained image 105. In such implementations, the input generation engine 108 can obtain the image 105 and prepare the obtained image 105 for processing by the first machine learning model 110. In some implementations, the pre-processing operations can include processing the obtained image 105 to generate an input vector 108a. The generated input vector 108a can include a numerical representation of the obtained image 105. For example, the input vector 108a can include a plurality of fields that each correspond to a pixel of the obtained image 105. The input generation engine 108 can determine a numerical value for each of the fields that describes a corresponding pixel of the obtained image 105. The determined numerical values for each of the fields can be used to encode image features of the obtained image 105 into the generated input vector 108a. The generated input vector 108a, which numerically represents the obtained image 105, can be provided as an input to the first machine learning model 110. As the input vector 108a represent the obtained image 105, the input vector 108a can be referred to as image data.

However, in some implementations, the input generation engine 108 may perform different operations or not be required at all. For example, in some implementations, the input generation engine 108 can make formatting changes to the obtained image 105 prior to inputting the image 105 into the first machine learning model 110. In such implementations, this can include removing header data or other metadata from the obtained image 105, adding header data or other metadata to the obtained image 105, modifying the file type or format of the obtained image 105, or other pre-processing operations. By way of another example, the computer 140 can provide the obtained image 105 for input to the first machine learning model 110 without performing pre-processing operations to format the obtained image 150. For example, in such implementations, the obtained image 105 may already be in a format expected by the first machine learning model 110 at the time the image 105 is obtained. That is, in some implementations, the obtained image 105 can be an image vector such as image vector 108a that represents the obtained image 105 and was previously generated.

Data representing the obtained image 105 such as the input data vector 108a can be provided, by the computer 140, as an input to the first machine learning model 110. The first machine learning model 110 is trained to segment the data representing the obtained image 110 to identify a portion of the obtained image 105 that corresponds to an image of a pancreas. In some implementations, the machine learning model 110 can include one or more deep neural networks that have been trained to process a CT image of an internal portion of a body and identify a portion of the CT image that corresponds to a pancreas. In some implementations, the first machine learning model 110 can include one or more deep neural networks. However, the present disclosure is not limited to the use of deep neural networks. Instead, any machine learning model that can trained or configured to segment data representing an image such as a CT image of an internal portion of a body to identify a pancreas can be used.

The machine learning model 110 can generate output data representing a second image 115. In some implementations, this second image 115 can include an image with each of the pixels labeled as a pancreas pixel or non-pancreas pixel. A pancreas pixel is a pixel that falls within a depiction of a pancreas in an image. A pixel that is non-pancreas pixel is a pixel of an image that falls outside of a depiction of pancreas in an image. In such implementations, the second image 115 can be provided to an output analysis module 110a that identifies a portion of the pixels of the second image 115 labeled as pancreas pixels, a region of pixels around the pixels of the second image 115 labeled pancreas pixels (including the pancreas pixels), or a subset of the pancreas pixels representing a portion of the depicted pancreas. Then the selected portion of the second image 115 can be output of the output analysis module 110a as output data 115a. The output data 115a may also be referred to as image data 115a. The second output data 115a, which represents a portion of the image data 108a depicting a pancreas or a portion thereof, can be provided as an input to the second machine learning model 120 and the third machine learning model 130.

The first machine learning model 110 can be trained in a number of different ways. In one implementation, the first machine learning model 110 can be trained to distinguish between pancreas pixels and non-pancreas pixels, and then output, based on a number of spatially related pancreas pixels detected, a likelihood that at least a portion of the image data 108a represents a pancreas. In some implementations, such training can be achieved using a simulator to generate sample images depicting abdominal organs of an organism. Each pixel of the sample image can be labeled as depicting a pancreas or not depicting a pancreas.

In such implementations, each training image can be provided as an input to the first machine learning model 110 during training, be processed by the first machine learning model 110, and then training output generated by the first machine learning model 1110 can be used to determine a predicted label for each pixel of the training image. The predicted label for each pixel can be compared to a training label for a corresponding pixel of the sample (or training) image. Then, the parameters of the first machine learning model 110 can be adjusted based on differences between the predicted labels and the training labels. This iterative process can continue for each of a plurality of training images until predicted pixel labels produced by the first machine learning model 110 for a training image match, within a predetermined level of error, training labels generated by the simulator for the training images. Though the uses of images generated by a simulator are used in this example to train the first machine learning model 110, actual images of actual pancreases can also be used.

As indicated above, the computer 140 can provide the output data 115a, which represents a portion of the image data 108 depicting a pancreas, as an input to a second machine learning model 120. The second machine learning model 120 can be trained to process the output data 115a and classify the output data 115a as being an image data that depicts a pancreas that is normal, abnormal with pancreatic ductal adenocarcinoma (PDAC), abnormal with pancreatic neuroendocrine tumors (PanNet), or abnormal with Cyst. In one implementation, the second machine learning model 120 can be implemented using a random forest algorithm with radiomic features that has been trained to classify an image of a pancreas as normal, abnormal with PDAC, abnormal with PanNet, or abnormal with Cyst. However, the second machine learning model 120 of the present disclosure is not limited to a random forest algorithm. Instead, any machine learning model that has been trained or configured to classify an image of a pancreas as normal, abnormal with PDAC, abnormal with PanNet, or abnormal with Cyst can be used. The output 125 generated by the second machine learning model can include data 125 that indicates a classification of the pancreas as normal, abnormal with PDAC, abnormal with PanNet, or abnormal with Cyst.

The second machine learning model 120 can be trained in a number of different ways. In one implementation, the second machine learning model 110 can be trained to distinguish between image data that depicts a normal pancreas, image data that depicts an abnormal pancreas with PDAC, image data that depicts an abnormal pancreas with PanNET, and image data that depicts an abnormal pancreas with Cyst. In some implementations, such training can be achieved using a simulator to generate a plurality of sample images that each depict a pancreas in one of the aforementioned states—i.e., normal/healthy, abnormal with PDAC, abnormal with PanNET, or abnormal with Cyst. Each of the sample images can be labeled based on the state of the pancreas depicted. In some implementations, the labels can include normal, PDAC, PanNET, or Cyst. However, the present disclosure is not limited to such particular label. Instead, any label can be used to represent the different pancreas states. For example, in some implementations, a number 1 can be used to represent normal, a number 2 can be used to represent PDAC, a number 3 can be used to represent PanNET, and a number 4 can be used to represent Cyst. Other labels can also be used.

In such implementations, each training image can be provided as an input to the second machine learning model 120 during training, be processed by the second machine learning model 120, and then training output generated by the second machine learning model 120 can be used to determine a predicted class or label for each processed image. The predicted class or label for each processed image can be compared to a training label for the processed image. Then, the parameters of the second machine learning model can be adjusted based on differences between the predicted label and the training label. This iterative process can continue for each of a plurality of training images until a predicted class or label produced by the second machine learning model 120 for a training image match, within a predetermined level of error, a training class or label generated by the simulator for the training image.

Simulated image can be particular beneficial for training the second machine learning model 120. This is because the available pool of training images for the second machine learning model 120 may be in short supply, as conventional methods for early detection of pancreatic cancer may not catch pancreatic cancer at its onset due to the small size of the neoplasms. Thus, a patient may have pancreatic cancer in its early stages but not have a CT scan, or other imaging scan, to capture an image of the abnormal pancreas. Though the use of images generated by a simulator are used in this example to train the second machine learning model 120, actual images of actual pancreases can also be used.

In some implementations, the features of training images generated by the simulator may be customizable by a user of the system 100. For example, a user can input one or more parameters that describe the number of neoplasms to be rendered in a sample image of a simulated pancreas, a size of one or more neoplasms to be rendered in a sample image of a simulated pancreas, a location of one or more neoplasms to be rendered in a sample image of a simulated pancreas, or a combination thereof. The simulator can then generate training images for use in training the second machine learning model 120 based on the one or more parameters.

The computer 140 can provide (i) the output data 115a derived from output data of the first machine learning model 110, which depicts a pancreas or portion thereof, and (ii) the output data 125 that indicates a classification of the pancreas as normal, abnormal with PDAC, abnormal with PanNet, or abnormal with Cyst as inputs to the third machine learning model 130. The third machine learning model 130 can be trained to detect and localize abnormalities of the pancreas depicted by the output data 115a. In some implementations, the third machine learning model 130 can be a deep neural network having multiple sub-processing engines. For example, the deep neural network can include a first sub-processing engine that has been trained to detect and localize PDAC tumors, a second sub-processing engine that has been trained to detect and localize dilated ducts, and a third sub-processing engine that has been trained to detect and localize PanNet tumors. Dilated ducts can be a PDAC indicator as a PDAC neoplasm such as a tumor can form in the duct and block the duct, which causes the duct to dilate. In some implementations, detection, in an image of a pancreas or portion thereof, of dilated ducts may be labeled as an abnormal PDAC pancreas.

In some implementations, one or more of the sub-processing engines can be selected based on the output data 125 indicating a classification of the pancreas depicted by output data 115a. In other implementations, the output data 115a can be processed through each of the sub-processing engines and each of the particular sub-processing engines can determine whether one or more neoplasms associated with the particular sub-processing engine is detected in the output data 115a. An example of a third machine learning model 130 is provided that includes a deep neural network. In such implementation, each of the one or more sub-processing engines can be implemented using a deep neural network. In other implementations, detection, in an image of pancreas or portion thereof, of dilated ducts may be labeled as a separate pancreas state such as abnormal with dilated ducts. In some implementations, each of the sub-processing engines may be implemented using separate deep neural networks or other separate machine learning models. In other implementations, the each sub-processing engine may correspond to a particular subset of a larger deep neural network. However, the present disclosure need not be so limited. Instead, any machine learning model can be used, once it is trained to perform the operations described above.

The output 135 generated by the third machine learning model 130 can include (i) data indicating that the pancreas is normal or (b) data indicating a likely location of one or more pancreatic neoplasms. Data indicating a likely location of one or more pancreatic neoplasms can be generated in a variety of ways. The output data 135 can be provided to a post-processing engine 180 for interpretation.

The third machine learning model 130 can be trained in a number of different ways. In one implementation, the third machine learning model 130 can be trained to distinguish between whether image data of pancreas, or portion thereof, depicts (i) a normal pancreas or (ii) location information describing a location of one or more neoplasms on the pancreas. In some implementations, such training can be achieved using sample images of pancreas or portion thereof, generated by a simulator such as the images generated to train the second machine learning model 120. For example, the simulator can be used to generate a plurality of sample images that each depict a pancreas in one of the aforementioned states—i.e., normal/healthy, abnormal with PDAC, abnormal with PanNET, abnormal with Cyst, or abnormal with dilated ducts. Or these images can be accessed from a database 170 of previously generated images. Each image can be labeled (i) with a location of any neoplasms on the depicted pancreas or (ii) with a label indicating the pancreas depicted has no neoplasms, a label indicating that the depicted pancreas is normal, or a combination thereof.

In such implementations, each training image and data describing the stage of the pancreas depicted by the training image can be provided as an input to the third machine learning model 130 during training, be processed by the third machine learning model 130, and then training output generated by the third machine learning model 130 can be used to determine a predicted label for each processed image. The predicted label for each processed image can be compared to a training label for the processed image. In this instance, that can include comparing training label(s) (i) indicating a location of any neoplasms in the pancreas of the training image or (ii) indicating that the that the pancreas depicted by the training image is normal (e.g., a pancreas that does not include a neoplasm). Then, the parameters of the third machine learning model can be adjusted based on differences between the predicted label and the training label. This iterative process can continue for each of a plurality of training images until a predicted label produced by the third machine learning model 130 for a training image match, within a predetermined level of error, a training label generated by the simulator for the training image. Though the uses of images generated by a simulator are used in this example to train the third machine learning model 130, actual images of actual pancreases can also be used.

The post-processing engine 180 can process the output data 135 generated by the third machine learning model 130 and make one or more inferences based on the processing. Data 180a describing these inferences can be output using a user interface of the computer 140, the CT Scanner 150, other image scanner, or some other computer for interpretation by a human user. The user interface can be a visual interface such as display, an audio interface such as a speaker, a haptic feedback interface, or a combination there.

In some implementations, for example, the post-processing engine 180 can obtain the output data 135 and analyze the output data 135. The post-processing module can determine that the output data 135 includes an image depicting the pancreas (or portion thereof) of image data 115a that includes visual modifications such as highlights or shading in one or more colors that indicates the locations of one or more pancreatic neoplasms on the depicted pancreas. In such implementations, the post-processing engine 180 can generate rendering data 180a that, when processed by one or more computers, can cause the one or more computers to render a visualization of the pancreas with the highlights on a display of the one or more computers. The one or more computers can include the computer 140, the CT scanner 150, other image scanner, or other computer. If the post-processing engine 180 determines, based on the output data 135, that the pancreas is normal (e.g., no detected neoplasms), then the post-processing engine 180 can generate output data 180a that, when processed by one or more computers, can cause the one or more computers to display data indicating that the pancreas is normal. In some implementations, this can include generating and providing rendered data to the computer 140, the CT scanner 150, other image scanner, or other computer that, when processed by the computer 140, the CT scanner 150, the image scanner, or the other computer, causes the computer 140, the CT scanner 150, the other image scanner, or the other computer to display a pancreas with no highlighting, which indicates no pancreas neoplasms were detected.

In other implementations, if the post-processing engine 180 determines, based on the output data 135, that the pancreas includes one or more neoplasms, then the post-processing engine 180 can generate, based on the output data 135, data 180a that can be used to generate, display, or otherwise output, a textual report that describes the location of one or more pancreatic neoplasms on the pancreas. The textual report can be displayed on a display of a computer or read out of a speaker by using text-to-speech conversion engine to convert the text words into spoken words output using a speaker. The display or speaker can be part of the computer 140, the CT scanner 150, other image scanner, or other computer. Alternatively, if the post-processing engine 180 determines, based on the output data 135, that no pancreatic neoplasms were present, then the post-processing engine 180 can generate data 180a that causes another computer or scanner to generate textual data such as a notification or other visualization on a display, spoken words via a speaker, haptic feedback, or a combination thereof, indicating that a normal pancreas is depicted by the input image data 105.

In yet other implementations, if the post-processing engine 180 determines, based on the output data 135, that the pancreas includes one or more neoplasms, then the post-processing engine 180 can generate, based on the output data 135, machine readable code 180a that can be, interpreted by the computer 140, the CT scanner 150, other image scanner, or other computer, as describing the location of one or more pancreatic neoplasms on a pancreas. In such instances, for example, the post-processing engine 180 can generate rendering based on the output data 135 that, when rendered by the one or more computers such as the computer 140, the CT scanner, other image scanner, or other computer, causes the one or more computers to output a visual model of the pancreas that depicts the locations of the pancreatic neoplasms using one or more colors. In some implementations, the visual model can be a 3-D displayed on a user display, a 3-D holographic model generated in an open space using one or more holographic projectors, or the like. Alternatively, if the post-processing engine 180 determines, based on the output data 135, that no pancreatic neoplasms were present, then the post-processing engine 180 can generate data 180a that causes another computer or scanner to generate textual data such as a notification or other visualization on a display, spoken words via a speaker, haptic feedback, or a combination thereof, indicating that a normal pancreas is depicted by the input image data.

In some implementations, the post-processing engine 180 can used to perform additional analysis that does not relate output of the results of the system 100. For example, in some implementations, the post-processing engine 180 can be used to evaluate the geometry of any neoplasms detected by the cascaded set of machine learning models and represented by output data 135 (e.g., labeled image data depicted neoplasms on the pancreas) to determine whether detected neoplasms are potentially cancerous. For example, if the post-processing engine 180 determine that the detected neoplasms have a first geometry, then the post-processing engine 180 can determine that the detected neoplasms are cancerous. Alternatively, if the post-processing engine 180 determines that the detected neoplasms have a second geometry, then the post-processing engine 180 can determine that the detected neoplasms are not cancerous. Then, the post-processing engine 180 can generate output data 180a that, when processed by the computer 140, the CT scanner 150, other image scanner, or other computer, causes the computer to output data indicating that the neoplasms were cancerous or not cancerous based on the geometry of the neoplasms. Such output data can be in visual form, audio form, textual form, haptic form, or any combination thereof.

Figure 2:
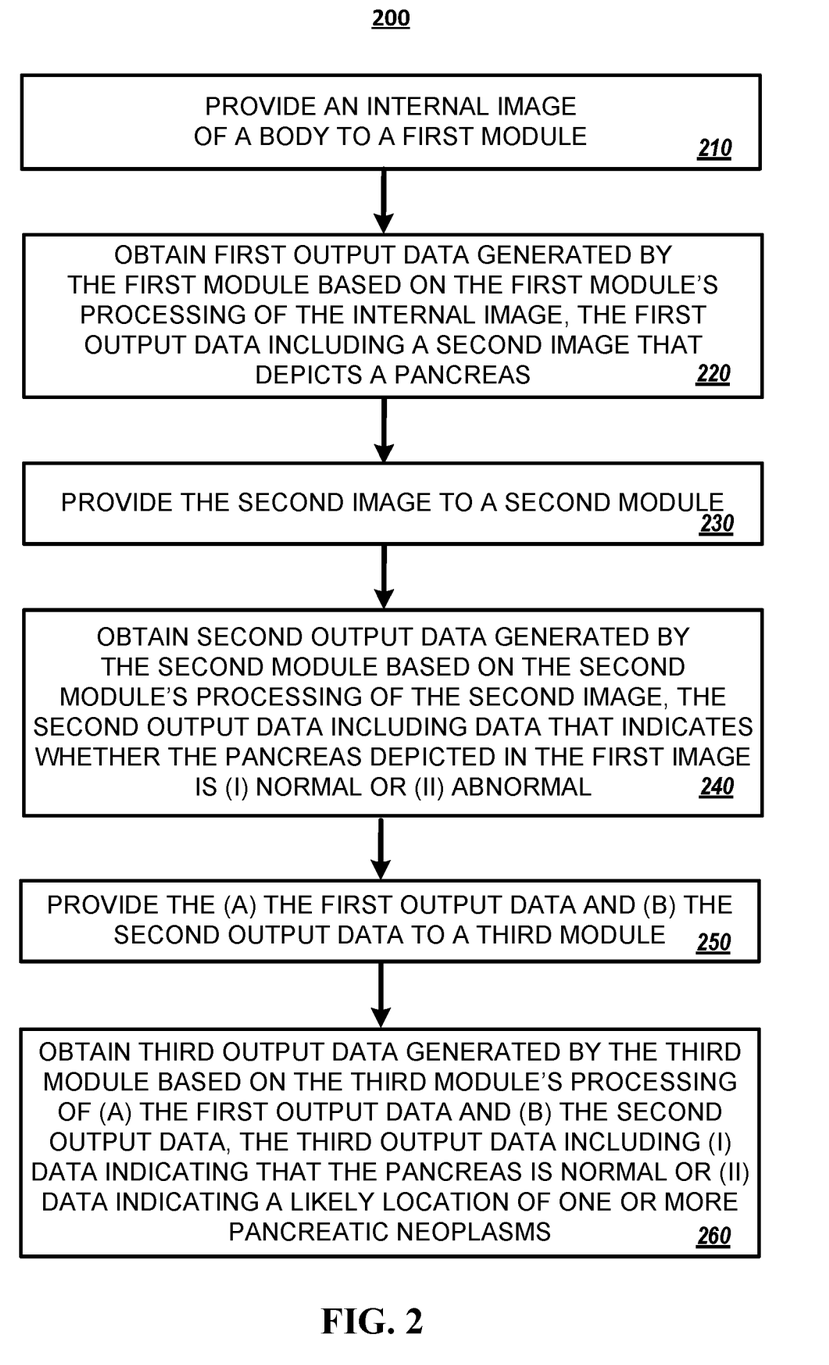
FIG. 2 is flowchart of an example of a process for using cascaded machine learning models to facilitate early detection of pancreatic neoplasms.

FIG. 2 is flowchart of an example of a process 200 for using cascaded machine learning models to facilitate early detection of pancreatic neoplasms. In general, the process 200 includes providing, by one or more computers, a first image to a first processing engine (210), obtaining, by the one or more computers, first output data generated by the first processing engine based on the first processing engine's processing of the first image, the first output data including a second image that depicts a pancreas (220), providing, by the one or more computers, the second image to a second processing engine, (230), obtaining, by the one or more computers, second output data generated by the second processing engine based on the second processing engine's processing of the second image, the second output data including data that indicates whether the pancreas depicted by the first image is (i) normal or (ii) abnormal (240), providing, by the one or more computers, (a) the first output data and (b) the second output data to a third processing engine (250), and obtaining, by the one or more computers, third output data generated by the third processing engine based on the third processing engine's processing of (a) the first output data and (b) the second output data, the third output data including (I) data indicating that the pancreas is normal or (II) data indicating a likely location of one or more pancreatic neoplasms (260).

Figure 3:
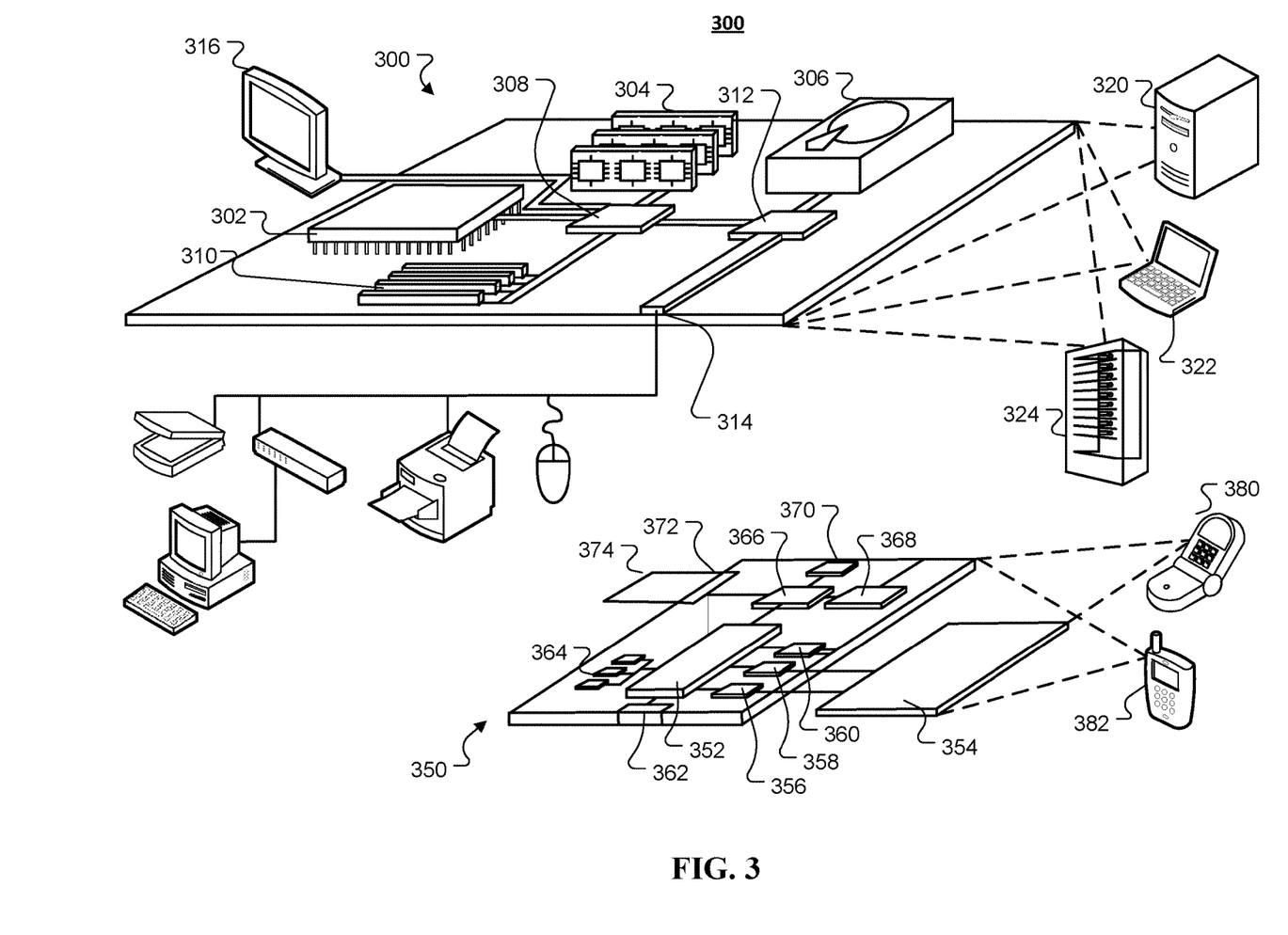
FIG. 3 is a block diagram of system components that can be used to implement a system for using cascaded machine learning models to facilitate early detection of pancreatic neoplasms.

FIG. 3 is a block diagram of system 300 components that can be used to implement a system for using cascaded machine learning models to facilitate early detection of pancreatic neoplasms.

Computing device 300 is intended to represent various forms of digital computers, such as laptops, desktops, workstations, personal digital assistants, servers, blade servers, mainframes, and other appropriate computers. Computing device 350 is intended to represent various forms of mobile devices, such as personal digital assistants, cellular telephones, smartphones, and other similar computing devices. Additionally, computing device 300 or 350 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 300 includes a processor 302, memory 304, a storage device 306, a high-speed interface 308 connecting to memory 304 and high-speed expansion ports 310, and a low speed interface 312 connecting to low speed bus 314 and storage device 306. Each of the components 302, 304, 306, 308, 310, and 312, are interconnected using various busses, and can be mounted on a common motherboard or in other manners as appropriate. The processor 302 can process instructions for execution within the computing device 300, including instructions stored in the memory 304 or on the storage device 308 to display graphical information for a GUI on an external input/output device, such as display 316 coupled to high speed interface 308. In other implementations, multiple processors and/or multiple buses can be used, as appropriate, along with multiple memories and types of memory. Also, multiple computing devices 300 can be connected, with each device providing portions of the necessary operations, e.g., as a server bank, a group of blade servers, or a multi-processor system.

The memory 304 stores information within the computing device 300. In one implementation, the memory 304 is a volatile memory unit or units. In another implementation, the memory 304 is a non-volatile memory unit or units. The memory 304 can also be another form of computer-readable medium, such as a magnetic or optical disk.

The storage device 308 is capable of providing mass storage for the computing device 300. In one implementation, the storage device 308 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 304, the storage device 308, or memory on processor 302.

The high-speed controller 308 manages bandwidth-intensive operations for the computing device 300, while the low speed controller 312 manages lower bandwidth intensive operations. Such allocation of functions is only an example. In one implementation, the high-speed controller 308 is coupled to memory 304, display 316, e.g., through a graphics processor or accelerator, and to high-speed expansion ports 310, which can accept various expansion cards (not shown). In the implementation, low-speed controller 312 is coupled to storage device 308 and low-speed expansion port 314. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 300 can be implemented in a number of different forms, as shown in the figure. For example, it can be implemented as a standard server 320, or multiple times in a group of such servers. It can also be implemented as part of a rack server system 324. In addition, it can be implemented in a personal computer such as a laptop computer 322. Alternatively, components from computing device 300 can be combined with other components in a mobile device (not shown), such as device 350. Each of such devices can contain one or more of computing device 300, 350, and an entire system can be made up of multiple computing devices 300, 350 communicating with each other.

The computing device 300 can be implemented in a number of different forms, as shown in the figure. For example, it can be implemented as a standard server 320, or multiple times in a group of such servers. It can also be implemented as part of a rack server system 324. In addition, it can be implemented in a personal computer such as a laptop computer 322. Alternatively, components from computing device 300 can be combined with other components in a mobile device (not shown), such as device 350. Each of such devices can contain one or more of computing device 300, 350, and an entire system can be made up of multiple computing devices 300, 350 communicating with each other.

Computing device 350 includes a processor 352, memory 364, and an input/output device such as a display 354, a communication interface 366, and a transceiver 368, among other components. The device 350 can also be provided with a storage device, such as a micro-drive or other device, to provide additional storage. Each of the components 350, 352, 364, 354, 366, and 368, are interconnected using various buses, and several of the components can be mounted on a common motherboard or in other manners as appropriate.

The processor 352 can execute instructions within the computing device 350, including instructions stored in the memory 364. The processor can be implemented as a chipset of chips that include separate and multiple analog and digital processors. Additionally, the processor can be implemented using any of a number of architectures. For example, the processor 310 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 350, such as control of user interfaces, applications run by device 350, and wireless communication by device 350.

Processor 352 can communicate with a user through control interface 358 and display interface 356 coupled to a display 354. The display 354 can be, for example, a TFT (Thin-Film-Transistor Liquid Crystal Display) display or an OLED (Organic Light Emitting Diode) display, or other appropriate display technology. The display interface 356 can comprise appropriate circuitry for driving the display 354 to present graphical and other information to a user. The control interface 358 can receive commands from a user and convert them for submission to the processor 352. In addition, an external interface 362 can be provided in communication with processor 352, so as to enable near area communication of device 350 with other devices. External interface 362 can provide, for example, for wired communication in some implementations, or for wireless communication in other implementations, and multiple interfaces can also be used.

The memory 364 stores information within the computing device 350. The memory 364 can be implemented as one or more of a computer-readable medium or media, a volatile memory unit or units, or a non-volatile memory unit or units. Expansion memory 374 can also be provided and connected to device 350 through expansion interface 372, which can include, for example, a SIMM (Single In Line Memory Module) card interface. Such expansion memory 374 can provide extra storage space for device 350, or can also store applications or other information for device 350. Specifically, expansion memory 374 can include instructions to carry out or supplement the processes described above, and can also include secure information. Thus, for example, expansion memory 374 can be provided as a security module for device 350, and can be programmed with instructions that permit secure use of device 350. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 364, expansion memory 374, or memory on processor 352 that can be received, for example, over transceiver 368 or external interface 362.

Device 350 can communicate wirelessly through communication interface 366, which can include digital signal processing circuitry where necessary. Communication interface 366 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 368. In addition, short-range communication can occur, such as using a Bluetooth, Wi-Fi, or other such transceiver (not shown). In addition, GPS (Global Positioning System) receiver module 370 can provide additional navigation- and location-related wireless data to device 350, which can be used as appropriate by applications running on device 350.

Device 350 can also communicate audibly using audio codec 360, which can receive spoken information from a user and convert it to usable digital information. Audio codec 360 can likewise generate audible sound for a user, such as through a speaker, e.g., in a handset of device 350. Such sound can include sound from voice telephone calls, can include recorded sound, e.g., voice messages, music files, etc. and can also include sound generated by applications operating on device 350.

The computing device 350 can be implemented in a number of different forms, as shown in the figure. For example, it can be implemented as a cellular telephone 380. It can also be implemented as part of a smartphone 382, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

OTHER EMBODIMENTS

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method for detecting pancreatic neoplasms using cascaded machine learning models, the method comprising:
   providing first input data to a first machine learning model, the first input data including data representing an image;
   obtaining first output data generated by the first machine learning model based on the first machine learning model's processing of the first input data, the first output data representing a portion of the image that depicts a pancreas;
   providing second input data to a second machine learning model, the second input data including the data representing a portion of the image that depicts the pancreas;
   obtaining second output data generated by the second machine learning model based on the second machine learning model's processing of the second input data, the second output data representing data that indicates whether the depicted pancreas is (i) normal or (ii) abnormal;
   providing third input data to a third machine learning model, the third input data including (i) the data representing a portion of the image that depicts the pancreas and (ii) the data that indicates whether the depicted pancreas is (i) normal or (ii) abnormal;

obtaining third output data generated by the third machine learning model, the third output data including (a) data indicating that the pancreas is normal or (b) data indicating a likely location of one or more pancreatic neoplasms;

determining, based on the third output data, a likely location of one or more pancreatic neoplasms; and generating data that, when rendered, causes a computer to output display of a visual model of the pancreas that visually highlights, using one or more colors, the likely locations of the one or more pancreatic neoplasms.

2. The method of claim 1,
wherein the first machine learning model is a deep neural network that has been trained to segment the image to identify a pancreas in the image.

3. The method of claim 1, wherein the second machine learning model is a random forest model that has been trained to classify an image of a pancreas as (i) normal or (ii) abnormal.

4. The method of claim 3, wherein the second machine learning model is a random forest model that has been trained to classify an image of a pancreas as (i) normal, (ii) abnormal with PDAC, (iii) abnormal with PanNet, or (iv) abnormal with Cyst.

5. The method of claim 1, wherein the data indicating whether the depicted pancreas is abnormal comprises (i) data indicating that the depicted pancreas is abnormal with PDAC or (ii) data indicating that the depicted pancreas is abnormal with PanNet.

6. The method of claim 5, wherein the second machine learning model is a random forest model that has been trained to classify an image of a pancreas as (i) normal, (ii) abnormal with PDAC, or (iii) abnormal with PanNet.

7. The method of claim 1, wherein the data indicating whether the depicted pancreas is abnormal comprises (i) data indicating that the depicted pancreas is abnormal with PDAC, (ii) data indicating that the depicted pancreas is abnormal with PanNet, or (iii) abnormal with Cyst.

8. The method of claim 1, wherein the third machine learning model is a deep neural network that has been trained to generate output data that includes (a) data indicating that the pancreas is normal or (b) data indicating a likely location of one or more pancreatic neoplasms.

9. A system for detecting pancreatic neoplasms using cascaded machine learning models comprising:
one or more computers and one or more storage devices storing instructions that are operable, when executed by the one or more computers, to cause the one or more computers to perform operations comprising:
providing first input data to a first machine learning model, the first input data including data representing an image;
obtaining first output data generated by the first machine learning model based on the first machine learning model's processing of the first input data, the first output data representing a portion of the image that depicts a pancreas;
providing second input data to a second machine learning model, the second input data including the data representing a portion of the image that depicts the pancreas;
obtaining second output data generated by the second machine learning model based on the second machine learning model's processing of the second input data, the second output data representing data that indicates whether the depicted pancreas is (i) normal or (ii) abnormal;

providing third input data to a third machine learning model, the third input data including (i) the data representing a portion of the image that depicts the pancreas and (ii) the data that indicates whether the depicted pancreas is (i) normal or (ii) abnormal;

obtaining third output data generated by the third machine learning model, the third output data including (a) data indicating that the pancreas is normal or (b) data indicating a likely location of one or more pancreatic neoplasms;

determining, based on the third output data, a likely location of one or more pancreatic neoplasms; and generating data that, when rendered, causes a computer to output display of a visual model of the pancreas that visually highlights, using one or more colors, the likely locations of the one or more pancreatic neoplasms.

10. The system of claim 9,
wherein the first machine learning model is a deep neural network that has been trained to segment the image to identify a pancreas in the image.

11. The system of claim 9, wherein the second machine learning model is a random forest model that has been trained to classify an image of a pancreas as (i) normal or (ii) abnormal.

12. The system of claim 9, wherein the data indicating whether the depicted pancreas is abnormal comprises (i) data indicating that the depicted pancreas is abnormal with PDAC or (ii) data indicating that the depicted pancreas is abnormal with PanNet.

13. The system of claim 12, wherein the second machine learning model is a random forest model that has been trained to classify an image of a pancreas as (i) normal, (ii) abnormal with PDAC, or (iii) abnormal with PanNet.

14. The system of claim 9, wherein the data indicating whether the depicted pancreas is abnormal comprises (i) data indicating that the depicted pancreas is abnormal with PDAC, (ii) data indicating that the depicted pancreas is abnormal with PanNet, or (iii) abnormal with Cyst.

15. The system of claim 14, wherein the second machine learning model is a random forest model that has been trained to classify an image of a pancreas as (i) normal, (ii) abnormal with PDAC, (iii) abnormal with PanNet, or (iv) abnormal with Cyst.

16. The system of claim 9, wherein the third machine learning model is a deep neural network that has been trained to generate output data that includes (a) data indicating that the pancreas is normal or (b) data indicating a likely location of one or more pancreatic neoplasms.

17. A non-transitory computer-readable medium storing software comprising instructions executable by one or more computers which, upon such execution, cause the one or more computers to perform operations comprising:
providing first input data to a first machine learning model, the first input data including data representing an image;
obtaining first output data generated by the first machine learning model based on the first machine learning model's processing of the first input data, the first output data representing a portion of the image that depicts a pancreas;
providing second input data to a second machine learning model, the second input data including the data representing a portion of the image that depicts the pancreas;
obtaining second output data generated by the second machine learning model based on the second machine learning model's processing of the second input data, the second output data representing data that indicates whether the depicted pancreas is (i) normal or (ii) abnormal;

providing third input data to a third machine learning model, the third input data including (i) the data representing a portion of the image that depicts the pancreas and (ii) the data that indicates whether the depicted pancreas is (i) normal or (ii) abnormal;

obtaining third output data generated by the third machine learning model, the third output data including (a) data indicating that the pancreas is normal or (b) data indicating a likely location of one or more pancreatic neoplasms;

determining, based on the third output data, a likely location of one or more pancreatic neoplasms; and generating data that, when rendered, causes a computer to output display of a visual model of the pancreas that visually highlights, using one or more colors, the likely locations of the one or more pancreatic neoplasms.

* * * * *